(12) United States Patent
Rezach et al.

(10) Patent No.: US 8,317,837 B2
(45) Date of Patent: Nov. 27, 2012

(54) CONNECTOR AND METHOD

(75) Inventors: William A Rezach, Atoka, TN (US);
Ryan R Davis, Plymouth, MN (US);
Grant D Foy, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 166 days.

(21) Appl. No.: 12/701,277

(22) Filed: Feb. 5, 2010

(65) Prior Publication Data
US 2011/0196425 A1 Aug. 11, 2011

(51) Int. Cl.
*A61B 17/70* (2006.01)
(52) U.S. Cl. ............ 606/267; 606/265; 606/277
(58) Field of Classification Search .......... 606/250–278, 606/324, 279; 403/96–97
See application file for complete search history.

(56) References Cited

U.S. PATENT DOCUMENTS

| | | | |
|---|---|---|---|
| 5,002,542 A | 3/1991 | Frigg | |
| 5,129,900 A | 7/1992 | Asher et al. | |
| 5,261,909 A | 11/1993 | Sutterlin et al. | |
| 5,282,801 A | 2/1994 | Sherman | |
| 5,344,422 A | 9/1994 | Frigg | |
| 5,487,744 A | 1/1996 | Howland | |
| 5,527,314 A | 6/1996 | Brumfield et al. | |
| 5,562,661 A * | 10/1996 | Yoshimi et al. | 606/264 |
| 5,611,800 A | 3/1997 | Davis et al. | |
| 5,643,263 A | 7/1997 | Simonson | |
| 5,662,651 A * | 9/1997 | Tornier et al. | 606/60 |
| 5,885,285 A | 3/1999 | Simonson | |
| 5,947,967 A | 9/1999 | Barker | |
| 5,976,135 A | 11/1999 | Sherman et al. | |
| 6,183,473 B1 | 2/2001 | Ashman | |
| 6,231,575 B1 | 5/2001 | Krag | |
| 6,248,104 B1 | 6/2001 | Chopin et al. | |
| 6,248,107 B1 | 6/2001 | Foley et al. | |
| 6,402,749 B1 | 6/2002 | Ashman | |
| 6,471,703 B1 | 10/2002 | Ashman | |
| 6,520,962 B1 | 2/2003 | Taylor et al. | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,872,209 B2 | 3/2005 | Morrison | |
| RE39,035 E | 3/2006 | Finn | |
| 7,066,939 B2 | 6/2006 | Taylor | |
| 7,261,715 B2 | 8/2007 | Rezach et al. | |
| 7,270,665 B2 | 9/2007 | Morrison et al. | |
| 7,377,922 B2 | 5/2008 | Barker | |
| 7,517,359 B2 | 4/2009 | Drewry et al. | |
| 7,575,587 B2 | 8/2009 | Rezach et al. | |
| 7,594,924 B2 * | 9/2009 | Albert et al. | 606/267 |
| 2002/0193794 A1 | 12/2002 | Taylor | |
| 2003/0139745 A1 | 7/2003 | Ashman | |
| 2003/0176862 A1 | 9/2003 | Taylor et al. | |

(Continued)

FOREIGN PATENT DOCUMENTS
EP 553424 A1 11/1992
(Continued)

*Primary Examiner* — Jan Christopher Merene (57) ABSTRACT

Embodiments of the invention include a device and method for securing linear elements relative to one another. In some embodiments, medical implant linear elements are secured in a connector by forcing one or both of the linear elements against at least another member such as a tapered member or wedge. The secured linear elements may include rods, posts, screws, hooks, bars, bolts, or other members.

16 Claims, 6 Drawing Sheets

U.S. PATENT DOCUMENTS

| | | |
|---|---|---|
| 2003/0191473 A1 | 10/2003 | Taylor |
| 2005/0234450 A1 | 10/2005 | Barker |
| 2006/0195096 A1* | 8/2006 | Lee et al. .................. 606/61 |
| 2006/0229611 A1* | 10/2006 | Avery et al. ................ 606/61 |
| 2006/0247624 A1* | 11/2006 | Banouskou et al. .......... 606/61 |
| 2007/0055239 A1* | 3/2007 | Sweeney et al. ............. 606/61 |
| 2008/0103507 A1* | 5/2008 | Purcell ...................... 606/103 |
| 2010/0160971 A1* | 6/2010 | Glerum et al. .............. 606/278 |
| 2010/0198260 A1* | 8/2010 | Gabelberger et al. ........ 606/264 |
| 2011/0172713 A1* | 7/2011 | Harper ....................... 606/264 |
| 2012/0029571 A1* | 2/2012 | Schwab et al. .............. 606/278 |
| 2012/0150232 A1* | 6/2012 | Van Nortwick et al. ..... 606/264 |

FOREIGN PATENT DOCUMENTS

| | | |
|---|---|---|
| EP | 786235 B1 | 1/1997 |
| EP | 982007 B1 | 8/1999 |
| FR | 2806902 A1 | 4/2000 |
| WO | 0167972 A2 | 2/2001 |

* cited by examiner

CONNECTOR AND METHOD

FIELD OF THE INVENTION

The present invention relates generally to the field of securing linear elements relative to one another, and more particularly relates to a device and method for securing medical implant linear elements relative to one another by forcing one or both of the linear elements against at least another member such as a tapered member or wedge.

BACKGROUND

Various pathologies of the human spine may be treated by stabilizing and properly positioning the vertebrae and joints of the spine. Some spinal implant systems rely on one or more rods as structural support for stabilizing and properly positioning components of the spine. Vertebral anchors such as bolts, screws, and hooks are typically secured to the vertebrae for connection to the one or more rods. These vertebral anchors must be positioned at various angles relative to the one or more rods to accommodate the anatomical structure of a patient, the physiological problem being treated, and the preference of the physician. It is difficult to provide secure connections between spinal support rods and vertebral anchors at all of the various angles that may be required, especially where there are different distances between rods and bolts and where components are located at different relative heights within the patient.

In some spinal implant systems, each vertebral anchor is connected to a rod with a connector. The connector attaches to a portion of a vertebral anchor and attaches to the rod. Example spinal systems are illustrated in U.S. Pat. Nos. 6,520,962 and 6,872,209, assigned to Warsaw Orthopedic, Inc., each of which is incorporated by reference herein in its respective entirety. The '962 patent, among other features, illustrates a "taper-lock" attachment of a connector to a vertebral anchor. The taper-lock attachment includes a tapered or wedge-shaped component against which the vertebral anchor is forced to secure the vertebral anchor relative to the connector. A wedged attachment such as this may provide a secure connection and have working components that are shielded from tissues by all or part of the body of a connector, and may be advantageous in some embodiments. A variety of other wedged attachments between a spinal rod and a connector are illustrated in connectors of the Medtronic TSRH® 3Dx™ System. These wedged attachments may also provide secure connections and have working components that are shielded from tissues by all or part of a connector, and may be advantageous in some embodiments. Wedged attachment mechanisms may also provide secure attachment with less material and may consume less volume than other mechanisms in some embodiments.

The '209 patent, among other features, illustrates a connector that includes an offset from the position of a vertebral anchor along the length of a rod. The offset, as disclosed in the '209 patent and understood by those skilled in the art, may be useful in some embodiments to reduce the profile of the spinal implant system relative to other spinal structures such as, but not limited to, the facet joints. The offset may be useful in some embodiments to displace a portion of the connector away from a vertebral anchor such that a patient's facet joint may be avoided, and therefore preserved.

A need exists for improved connectors that provide a combination of two or more of the features of wedged attachment structures for one or both linear elements, such as rods or vertebral anchors, and offset attachment of linear elements.

SUMMARY

One embodiment of the invention is a connector for coupling a first linear element to a second linear element. The connector may include a first portion through which an assembly axis passes and a first hole that is configured to receive at least a part of the first linear element. The first hole may also be offset from the assembly axis. The connector may also include a second portion through which the assembly axis passes and may be configured to receive at least a part of the second linear element. The second portion may be rotatable about the assembly axis relative to the first portion when the connector is in a first state and locked relative to the first portion when the connector is in a second state. The connector may also include an assembly that is positioned at least in part along the assembly axis within the first portion and the second portion, the assembly having an interference member distending from the assembly axis such that when the connector is in the first state, the interference member does not intersect the first hole in the first portion, and when the connector is in the second state, the interference member does at least in part intersect the first hole in the first portion. The connector may also include an actuator coupled to the second portion that is configured to transition the connector from the first state to the second state.

Another embodiment of the invention is a connector for coupling a first linear element to a second linear element. The connector includes a first portion through which an assembly axis passes, the first portion having a first hole that is configured to receive at least a part of the first linear element, and a second portion through which the assembly axis passes. The second portion may include a body, a second hole through the body transverse to the assembly axis, the second hole being configured to receive at least a part of the second linear element, the second hole being larger than the second linear element to allow for lateral movement of the second linear element within the second hole, and a locking component coupled to the body and capable of sliding relative to the body along the assembly axis and including at least one bearing surface that at least in part intersects the second hole. Directed lateral movement of the second linear element within the second hole may cause the second linear element to contact one or more of the at least one bearing surfaces and move the locking component along the assembly axis toward the first portion. The connector may also include an assembly that is positioned at least in part along the assembly axis within the first portion and the second portion and is able to slide a limited distance within at least the first portion. The assembly has an interference member that is capable of intersecting the first hole in the first portion when the assembly is slid in the first portion toward the second portion. The assembly is coupled between the first portion and the body of the second portion such that sliding separation of the first portion and the body of the second portion along the assembly axis is limited by the assembly. Movement of the locking component relative to the body of the second portion against the first portion may cause the limit of sliding separation between the first portion and the body of the second portion to be reached and cause the interference member to intersect the first hole in the first portion to thereby wedge the first linear element into a reentrant notch formed between the interference member and a wall of the first hole. The connector may also include an actuator coupled to the second portion and configured to push against the second linear element to cause directed lateral movement of the second linear element within the second hole and to move the locking component along the assembly axis toward the first portion, and to wedge the second linear element into a reentrant notch formed between the at least one bearing surface and a plane or tangent to a point of contact of the second hole to lock the second linear element relative to the second portion. The second portion may be rotatable about the assembly axis relative to the first portion when the locking component has not been moved toward the locking component along the assembly axis to engage the first portion.

Yet another embodiment of the invention is a system for spinal stabilization that may include one or more vertebral anchors for attaching to a vertebral body, one or more spinal rods for supporting a spinal structure, and one or more connectors for coupling the one or more vertebral anchors to the one or more spinal rods. At least one of the connectors may include a first portion through which an assembly axis passes, the first portion having a first hole that is configured to receive at least a part of a vertebral anchor. The vertebral anchor may be lockable within the first hole by a first wedge mechanism. At least one of the connectors may include a second portion through which the assembly axis passes, the second portion having a second hole that is configured to receive at least a part of a spinal rod. The spinal rod may be lockable within the second hole by a second wedge mechanism. At least one of the connectors may include an assembly that is positioned at least in part along the assembly axis and that couples the first portion to the second portion and allows limited separation between the first portion and the second portion. The first portion may be selectively lockable between a rotating condition and a locked condition about the assembly axis relative to the second portion. The first wedge mechanism may include a tapered surface such that as the first wedge mechanism is advanced toward a locked condition, space in which the vertebral anchor will be locked is both narrowed and shortened. The second wedge mechanism may include a tapered surface such that as the second wedge mechanism is advanced toward a locked condition, space in which the vertebral anchor will be locked is both narrowed and shortened.

DETAILED DESCRIPTION

Figure 1:
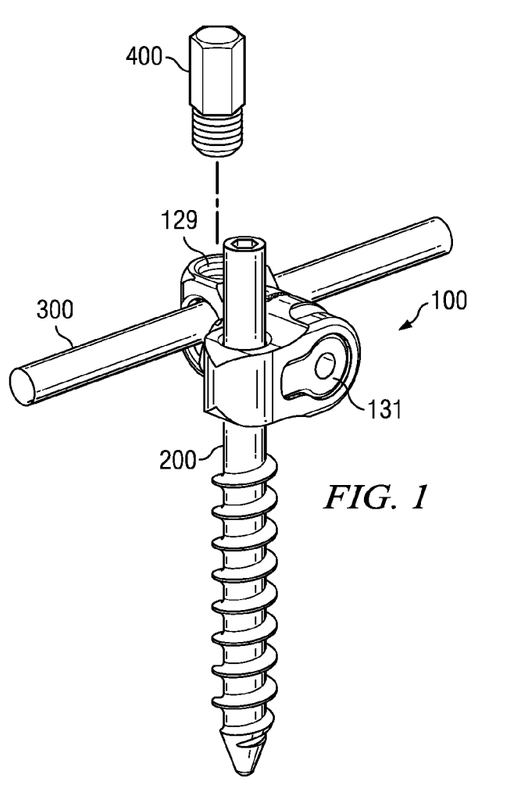
FIG. 1 is a partially exploded perspective view of an embodiment of a system for spinal stabilization.
Figure 2:
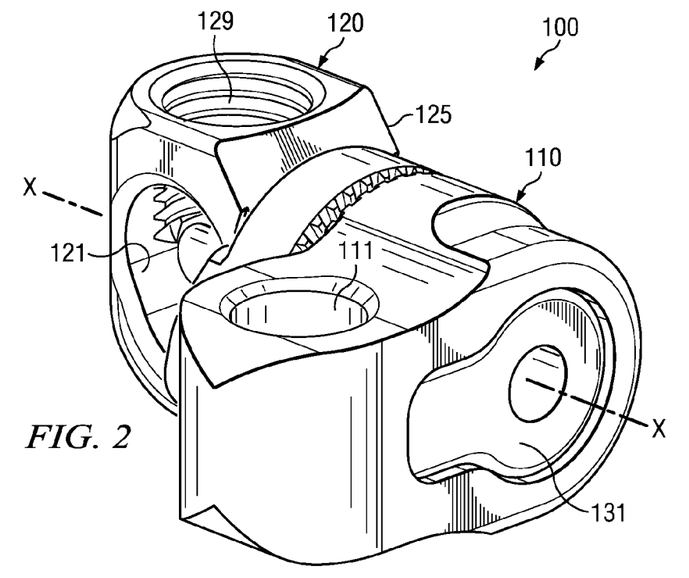
FIG. 2 is a perspective view of an embodiment of a connector for coupling linear elements.

An embodiment of a system for spinal stabilization is illustrated in FIG. 1. The system includes a connector 100, a first linear element 200 that is embodied in a vertebral screw, and a second linear element 300 that is embodied in a spinal rod. The illustrated system for spinal stabilization also includes a set screw 400 that is configured to be inserted in the threaded opening 129 in the connector 100. The connector 100 and its component parts are illustrated in greater detail in FIGS. 2-11. As used herein, the term linear element is used to refer to any element, component, or part to which a connector may be applied. For example and without limitation, linear elements may include rods, posts, screws, hooks, bars, bolts, or other members that may or may not be fully linear in shape. That is, a component may also be a "linear element," as used herein, if some part of the component is linear or elongated such that it could be fit within or grasped by any connector.

As shown collectively and in parts in FIGS. 1-11, the connector 100 includes a first portion 110, a second portion 120, and an assembly 130. As illustrated in FIGS. 2, 3, 4C, and 11 an assembly axis X passes through the first portion 110 and the second portion 120. The first portion 110 is shown with a first hole 111 that is configured to receive at least a part of the first linear element 200. As shown in FIG. 1, the first hole 111 receives a part of the proximal end of a bone screw that embodies the first linear element 200. As noted above, the first linear element 200 may be any of a variety of other components. A first hole or opening in the first portion of some embodiments may be a hook, cavity, partial ring or other opening that is less than a fully enclosed hole. The first hole 111 in the embodiment depicted is offset from the assembly axis X.

In some embodiments, the offset of the center of the first hole 111 from the assembly axis X is between about 5 mm and 20 mm. The center of the first hole is offset from the assembly axis X by about 7 mm to 12 mm in some embodiments. The embodiment shown in the FIG. 1 includes an offset of 8.75 mm. In still other embodiments, the offset of the first hole 111 from the assembly axis X may be any distance effective to accomplish a function of the device, including no offset. By way of further example, the offset may be useful to avoid intersecting with the facet joint of a patient when the connector 100 is used as a part of a posterior rod and screw system. An offset distance adequate to span a patient's facet is appropriate in that circumstance. Other uses may benefit from offsets of different amounts, each of which is contemplated by this disclosure.

Figure 3:
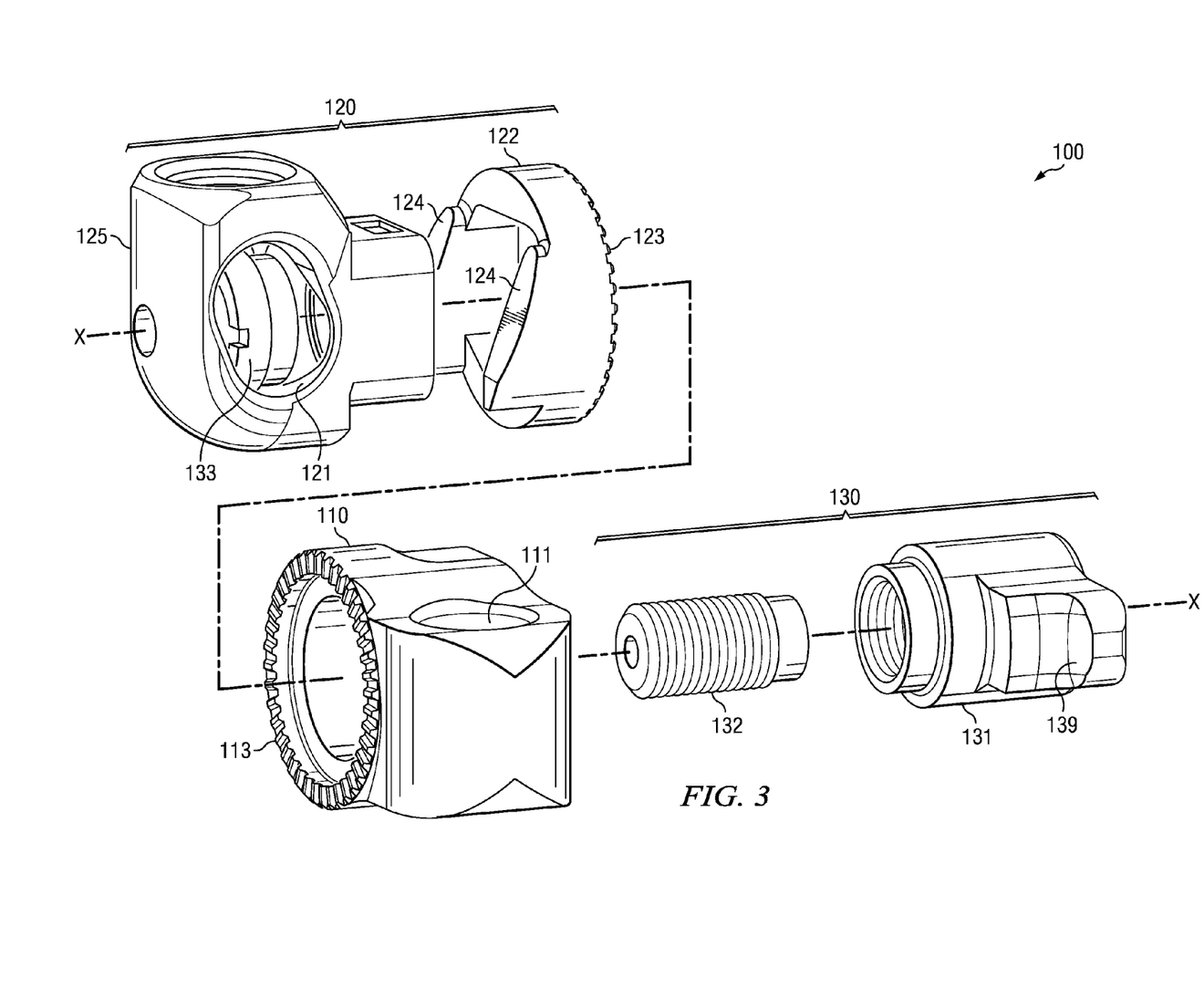
FIG. 3 is an exploded perspective view of the connector of FIG. 2.

In some embodiments, the first linear element 200, or any vertebral anchor located in the first hole 111, is lockable within the first hole 111 by a wedge mechanism. The first portion 110 of the connector 100 may also include teeth 113, as best illustrated in FIGS. 3 and 4C. The teeth 113 shown include peaks and valleys that radiate away from the assembly axis X and face toward the second portion 120. That is, each of the peaks and valleys respectively lies along a line radiating out from the assembly axis X, as seen in FIG. 4C. In other embodiments, teeth of another shape or other mechanisms to generate a high friction surface may be used. For example and without limitation, any surface of the first portion 110 may be roughened, contoured, knurled, tapered to include a morse taper, have an adhesive applied, or treated in any effective way to generate a higher friction surface and configured for contact with the second portion 120.

Figure 10:
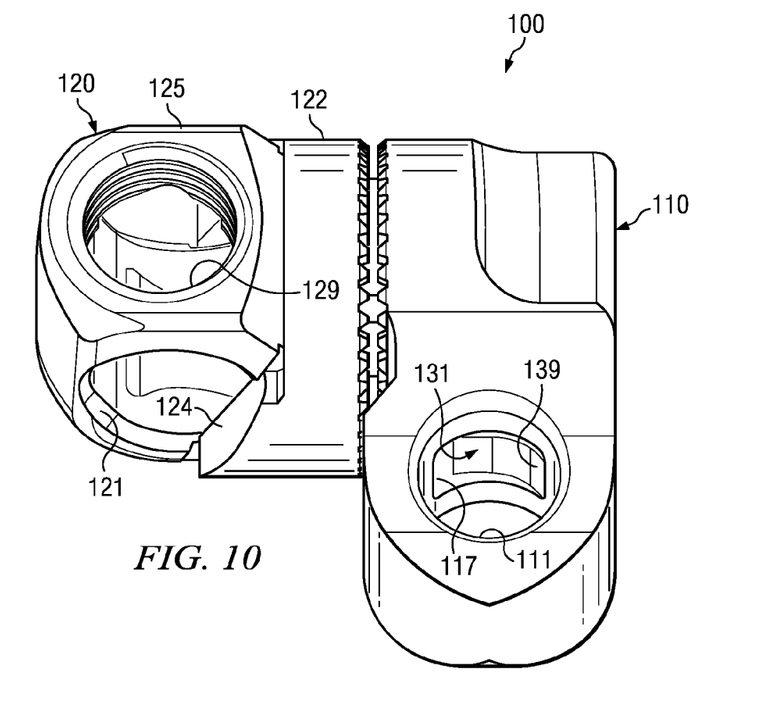
FIG. 10 is a perspective view of the connector of FIG. 2.
Figure 11:
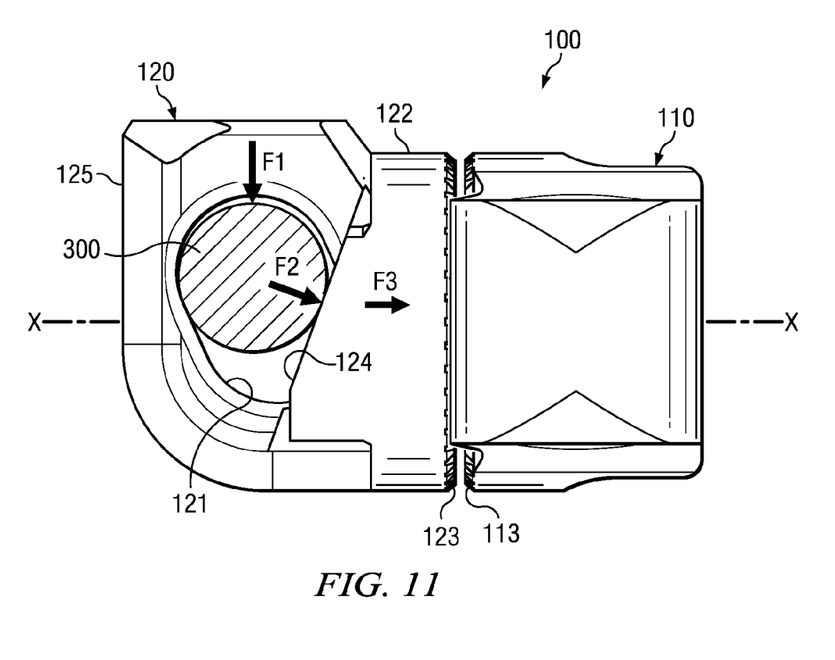
FIG. 11 is an elevation view of the connector of FIG. 2 with a linear element in the second hole shown in cross-section.

The second portion 120 is configured to receive at least a part of the second linear element 300, as shown in FIGS. 1 and 11. As noted above, the second linear element 300 may be any of a variety of other components. In the embodiment shown, the second portion 120 is rotatable about the assembly axis X relative to the first portion 110 when the connector 100 is in a first state. An example of this first state is shown in FIGS. 10 and 11, where the first portion 110 is disengaged from the second portion 120. In a second state, where the connector 100 has been actuated, and consequently where a washer 122, or locking component, of the second portion 120 has been moved against the first portion 110, the second portion 120 is locked relative to the first portion 110. In other embodiments, rotational locking between the first portion 110 and the second portion 120 may be achieved by any other effective mechanism.

Figure 6:
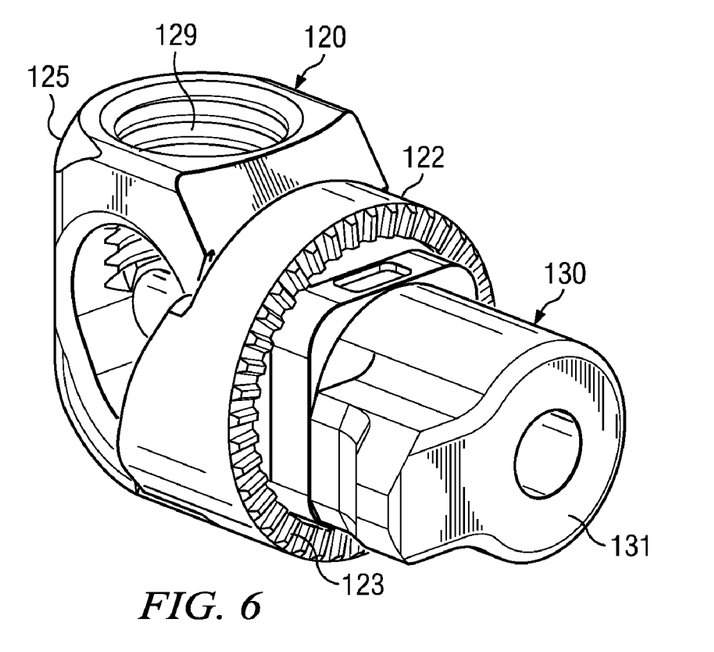
FIG. 6 is a perspective view of the second portion with the assembly of the connector of FIG. 2.
Figure 7:
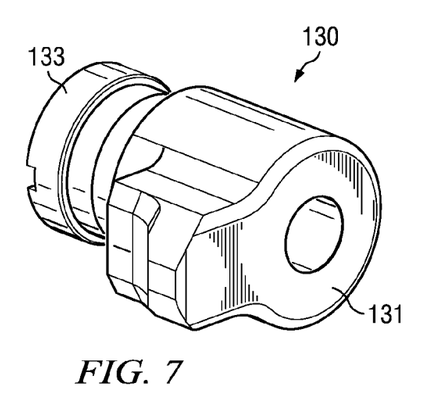
FIG. 7 is a perspective view of the assembly of the connector of FIG. 2.
Figure 9:
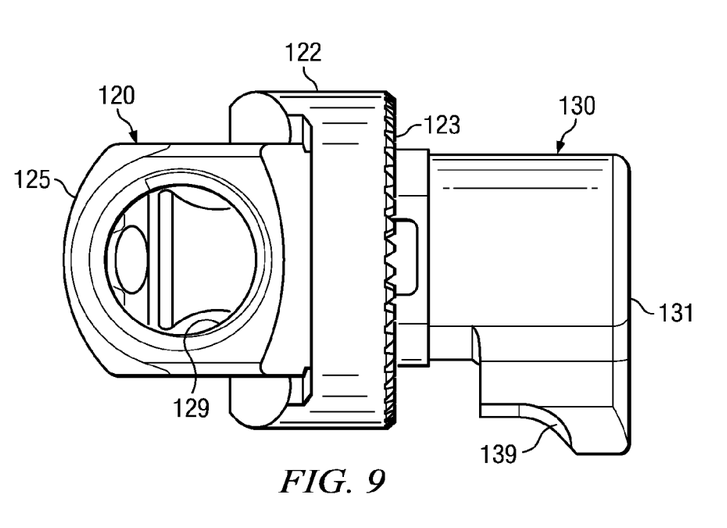
FIG. 9 is a plan view of the second portion with the assembly of the connector of FIG. 2.

The washer 122 shown in FIGS. 3, 6, and 9-11 substantially circumscribes the assembly axis X and is slidingly coupled to other parts, such as a body 125, of the second portion 120. By stating that the washer 122 "substantially circumscribes," it is intended that variations of a washer or other similar component which do not fully encircle the assembly axis X are also within the scope of the disclosure. In the illustrated embodiment, the washer 122 of the second portion 120 includes teeth 123, as best illustrated in FIGS. 3, 6, and 9, with peaks and valleys that radiate away from the assembly axis X and face toward the first portion 110. In some embodiments, teeth of the second portion may not be included on a separate washer, but may be integral with a unitary component or a different component of an alternate second portion.

The washer 122, or locking component, of the second portion 120 may include one or more ramps 124, as illustrated in FIGS. 3, 10, and 11. The ramps 124 shown intersect a second hole 121 in the second portion 120. Ramps, or bearing surfaces, of other embodiments may include any wedge, diagonal, or other similar surface that is capable of directing a force applied to an operative portion of the device, such as the ramps 124, to cause motion of the washer 122. In the illustrated embodiment, the motion of the washer 122 is primarily sliding motion relative to the body 125 toward portion 110. The second hole 121 shown is configured to receive at least a portion of the second linear element 300. In the embodiment shown in FIG. 11, the second linear element 300 is pressed against one or both of the ramps 124. In the illustrated embodiment, the ramps 124 are separated by a distance, but in other embodiments, there may be only one ramp or bearing surface, or there may be more than two. When the second linear element 300 is moved against the ramps 124, the washer 122 is urged to move along the assembly axis X relative to other parts, such as the body 125, of the second portion 120. The second hole 121 depicted is an oblong hole with a longer axis and a shorter axis that is transverse to the longer axis. The second hole 121 extends through the body 125 transverse to the assembly axis X. In the second portion 120 depicted, the longer axis of the illustrated oblong hole is oriented at an angle to the assembly axis X that is not a right angle. In other embodiments, the second hole may take a different shape. For example and without limitation, the hole may define a curved track, may be oval, or may just be round or nearly round with a larger diameter in at least one dimension than the linear element. A second hole of various embodiments that is larger than a captured linear element provides for directed lateral movement of a linear element within a second hole to cause relative motion between the part through which the second hole is made and a part that intersects the hole. The second hole may be oriented at any effective angle in combination with the ramps, wedges, or other components to urge a washer or similar locking component along the assembly axis X.

The assembly 130, as illustrated in FIGS. 3 and 5-10, is positioned at least in part along the assembly axis X within the first portion 110 in the second portion 120. The assembly 130 illustrated includes an interference member 131, an assembly bolt 132, and an assembly nut 133. Note that the assembly nut 133 is shown outside of the designated bracket for the assembly 130 in FIG. 3 so that the position of the assembly nut 133 once combined with the second portion 120 may be better illustrated. The assembly nut 133 as disclosed herein is nonetheless described as part of the assembly 130. The assembly 130 shown is able to slide at least a limited distance within the first portion 110. In some embodiments, the assembly 130 may also or alternatively slide within the second portion 120. The assembly 130 may be operated to adjust the length between the interference member 131 and the assembly nut 133. This adjustment allows for the forces applied to the first linear element 200 and the second linear element 300 to be regulated. For example, where the distance between the interference member 131 and the assembly nut 133 is relatively large, less clamping force will be applied to the first linear element 200 upon actuation of the connector 100. The assembly 130 may be adjustable throughout the period of use of the connector 100, or adjustment may be set by locking rotation of the assembly bolt 132 relative to one or both of the interference member 131 and the assembly nut 133 by any effective mechanism. For example and without limitation, threads may be crimped, an adhesive may be applied, or a weld, such as a laser weld or arc weld, may be applied.

The interference member 131 illustrated distends from the assembly axis X. When the connector 100 is in the first state where the first portion 110 is disengaged from the second portion 120, the interference member 131 does not intersect the first hole 111. This state is readily observed in FIG. 10. In the second state, where the connector 100 has been actuated, the interference member 131 is moved within the first portion 110 toward the second portion 120 which may cause the interference member 131 to at least in part intersect the first hole 111. In operation, movement from the first state to the second state of the illustrated embodiment includes sliding of the assembly 130 in the first portion 110 toward the second portion 120. The statement that sliding occurs, "toward the second portion 120" describes the direction of sliding of the assembly 130 within the first portion 110 and does not necessarily require any relative movement between the assembly 130 and the second portion 120. The assembly 130 shown, for example in FIGS. 3 and 6, when threaded together limits the sliding separation of the first portion 110 and the body 125 of the second portion 120. Separation is limited because the assembly nut 133 on one end of the assembly bolt 132 and the interference member 131 on the opposite end of the assembly bolt 132 attach respectively to the body 125 and the first portion 110. As the washer 122, or locking component, is pushed toward the first portion 110, the washer 122 pushes against the first portion 110 and moves the first portion 110 away from the second portion 120 until a limit of sliding separation is reached due to contact of the assembly washer 133 with the second portion 120. A shoulder or any other interfering part of an assembly and a second portion may provide a point of contact. The limit of sliding separation described in the illustrated embodiment then causes the interference member 131 to slide within the first portion 110 to intersect the first hole 111.

Figure 8:
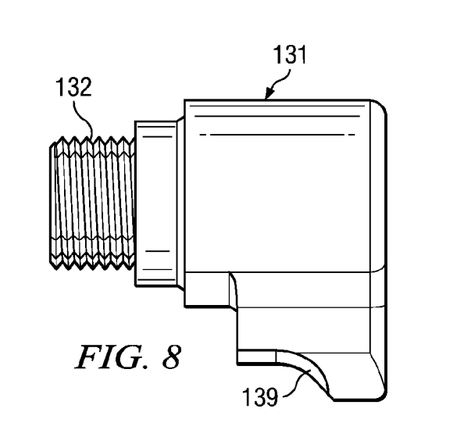
FIG. 8 is a plan view of part of the assembly of the connector of FIG. 2.

As most clearly seen in FIGS. 8-10, the interference member 131 includes a tapered part 139 where the interference member 131 is configured to intersect the first hole 111. The tapered part 139 may be angle, rounded, compound curved, or any other effective shape to bind or capture a linear element in the first hole 111. In some embodiments, the tapered part 139 may also include sharp, abrasive, adhesive, or other features to assist with capturing a linear element. An opening 117 in a wall of the first hole 111 is illustrated in FIGS. 4B and 10 through which the interference member 131 may access the first linear element 200.

In the illustrated embodiment, the first linear element 200 is wedged into a reentrant notch formed between the interference member 131 and a wall of the first hole 111. In particular, the first linear element 200 is wedged between one or more tangent points or a curved section of the wall of the first hole 111 and the tapered part 139 of the interference member 131. Stated another way for some embodiments, as the tapered part 139 is advanced across the first hole 111 and the connector is changed to a locked condition, the space in which a first linear element will be locked is both narrowed and shortened. As used for the illustrated embodiment, the terms narrowed and shortened mean smaller in two dimensions of a plane transverse to the first linear element being locked.

Figure 4A:
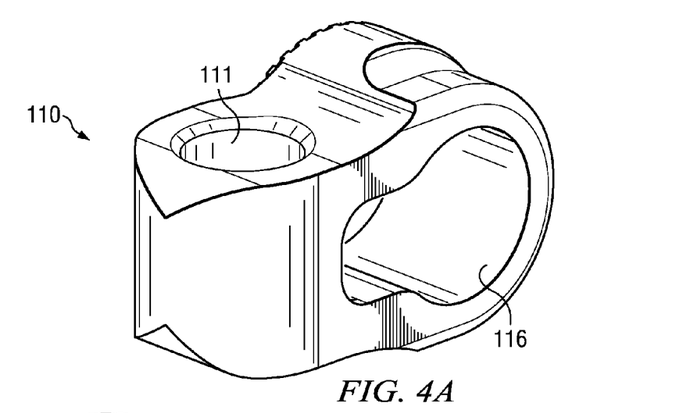
FIG. 4A-4C are perspective views of a first portion of the connector of FIG. 2
Figure 4B:
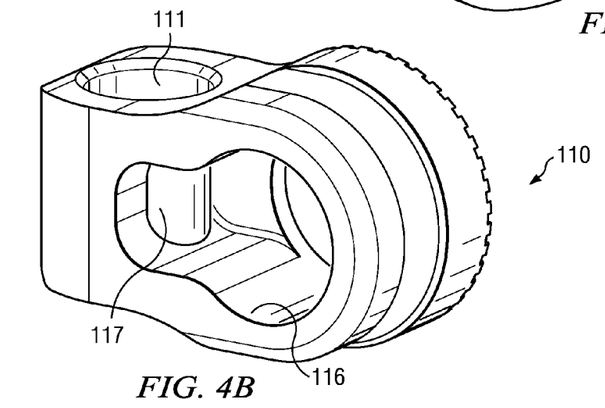
Figure 4C:
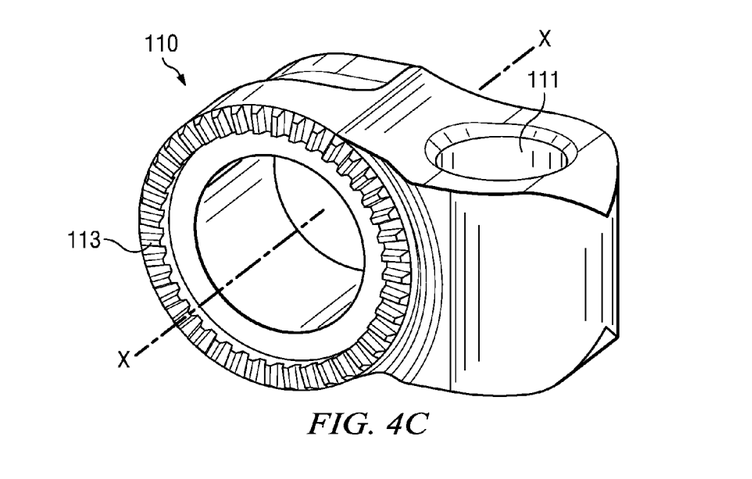
Figure 5:
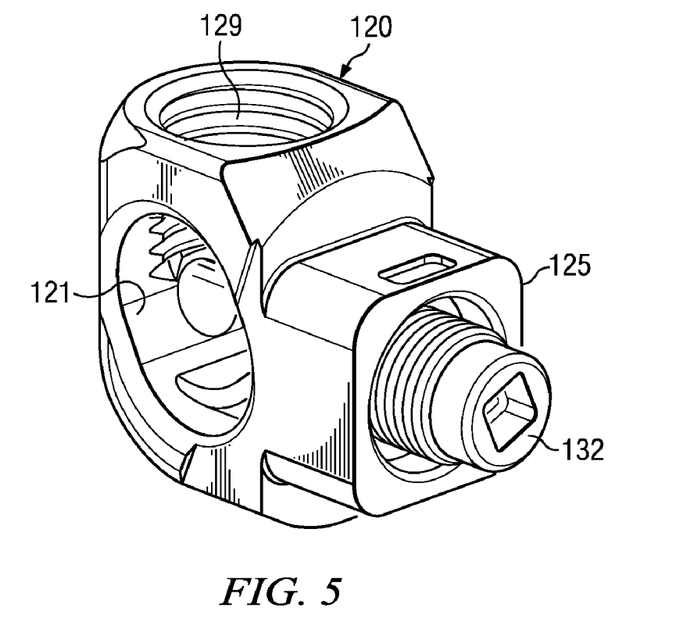
FIG. 5 is a perspective view of part of the second portion with part of the assembly of the connector of FIG. 2.

As shown in FIGS. 4A and 4B, an assembly opening 116 in the first portion 110 is keyed to prevent rotation of the interference member 131 of the assembly 130 relative to the first portion 110.

A set screw 400 is illustrated in FIG. 1 in position to be coupled to the second portion 120 in the threaded opening 129 of the connector 100. The set screw 400 shown serves as an actuator for the connector 100. The set screw 400 is configured to transition the connector 100 from the first state to the second state. The set screw 400 shown is a torque limiting break-off set screw. In other embodiments, any other effective device to apply an actuating force may be used. For example and without limitation, any other threaded fastener may be substituted for the set screw 400. Additionally, any other mechanism for applying an actuating force may be used, such as one or more cams, gears, ratchet mechanisms, or other effective devices. In the illustrated embodiment, the set screw 400 is configured to press against the second linear element 300 to urge the connector 100 from the first state to the second state. In particular, as depicted in FIG. 11, a downward force F1 applied to the second linear element 300 may transfer force and cause directed lateral movement of the second linear element 300 within the second hole 121. The second linear element 300 may transfer a component of force F2 through the ramp 124 into the washer 122. The washer 122 may then be translated relative to the body 125 along the assembly axis X with a component of force F3 toward the first portion 110. The second linear element 300 of the illustrated embodiment is wedged into a reentrant notch formed between the ramp 124 and one or more tangent points of contact, a plane, or a curve of the second hole 121 to lock the second linear element 300 relative to the second portion 120.

An embodiment of the invention is a connector for coupling a first linear element to a second linear element. The connector may include one or both of a body for coupling to the first linear element and a body for coupling to the second linear element. One or both of the coupling bodies may include wedged attachment structures having working components that are shielded from the tissues of a patient. Therefore, either or both of the wedged attachment structures may be actuated to couple to the first or second linear element without potentially damaging the tissues of a patient. The embodiment may further include an offset of the connection between the first linear element and the second linear element so that anatomical structures of a patient may be avoided.

Embodiments of the implant, including connector and linear elements in whole or in part, may be constructed of biocompatible materials of various types. Non-limiting examples of implant materials include titanium, titanium alloys, cobalt chrome alloys, stainless steel, ceramics, various plastics, plastic composites, non-reinforced polymers, reinforced polymers, carbon-reinforced polymer composites, PEEK, PEAK, and PEEK composites, and combinations thereof. If any trial instrument or implant is made from radiolucent material, radiographic markers can be located on the trial instrument or implant to provide the ability to monitor and determine radiographically or fluoroscopically the location of the implant. In some embodiments, the implant or individual components of the implant may be constructed of solid sections of bone or other tissues. Tissue materials include, but are not limited to, synthetic or natural autograft, allograft, or xenograft, and may be resorbable or non-resorbable in nature. Examples of resorbable materials that may be used include, but are not limited to, polylactide, polyglycolide, tyrosine-derived polycarbonate, polyanhydride, polyorthoester, polyphosphazene, calcium phosphate, hydroxyapatite, bioactive glass, and combinations thereof.

Another embodiment of the invention is a method of assembling a connector. The method may include providing a first portion through which an assembly axis passes, the first portion having a first hole that is configured to receive at least a part of the first linear element, and a second portion through which the assembly axis passes, the second portion configured to receive at least a part of the second linear element. The provided first portion may include an opening between the first hole and an interior part of the first portion. The provided connector may also include an assembly that is positioned at least in part along the assembly axis within the first portion in the second portion. The method may also include fixing the assembly through the first portion and the second portion such that the first portion and a second portion may only move apart for a limited distance, and wherein an interference member of the assembly is located in the first portion and in communication with the first hole through the opening, and wherein when the first portion is moved away from the second portion, the interference member is moved into the first hole.

Yet another embodiment of the invention is a method of engaging two wedged attachment structures of a connector with a single action. The method may include inserting a first linear element in a first portion of the connector and inserting a second linear element in a second portion of the connector, wherein the connector includes a wedged attachment structure in the first portion and a wedged attachment structure in the second portion. Another act of the method is to apply force to a part of the second portion to wedge the second linear element into the second portion. The act of applying force to the second linear element further operates the connector to wedge the first linear element into the first portion. In some embodiments, the act of operating the connector to wedge the first linear element into the first portion includes the act of wedging the first linear element into the first portion in a position offset from the second linear element.

The implant and system comprising the connector and linear elements shown in FIG. 1 may be implanted from a generally posterior approach for the purpose of stabilizing spinal anatomical structure. However, embodiments of the invention may include implantation from any surgical approach, or for other surgical purposes. Surgical approaches may include, but are not limited to, anterior, posterior, lateral, oblique, posterolateral, and anterolateral, or any combination of these and other approaches.

Various method embodiments of the invention are described herein with reference to particular medical implants. However, in some circumstances, each disclosed method embodiment may be applicable to each of the medical implants, or to some other implant operable as disclosed with regard to the various method embodiments.

The implant disclosed herein may be used in combination with other medical devices, including spinal fixation devices. Other medical devices with which the implant may be combined include, but are not limited to, interbody spinal implants, structural bone grafts, mesh, cages, spacers, staples, bone screws, plates, tethers of synthetic material or wires, and other spinal fixation instrumentation.

Terms such as anterior, posterior, height, length, narrow, short, toward, away, and the like have been used herein to note relative positions. However, such terms are not limited to specific coordinate orientations, but are used to describe relative positions referencing particular embodiments. Such terms are not generally limiting to the scope of the claims made herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

What is claimed is:

1. A connector for coupling a first ear element to a second linear element comprising:
   a first portion through which an assembly axis passes, the first portion having a first hole that is configured to receive at least a part of the first linear element, and wherein the first hole is offset from the assembly axis;
   a second portion through which the assembly axis passes, the second portion having a second hole configured to receive at least a part of the second linear element, and wherein the second portion is rotatable about the assembly axis relative to the first portion when the connector is in a first state and wherein the second portion is locked relative to the first portion when the connector is in a second state, the second portion includes a washer that substantially circumscribes the assembly axis and is slidingly coupled to other parts of the second portion, the washer includes one or more ramps that at least in part intersect the second hole in the second portion, wherein when the second linear element is pressed against the one or more ramps, the washer is urged to move along the assembly axis relative to the other parts of the second portion;
   an assembly that is positioned at least in part along the assembly axis within the first portion and the second portion, the assembly having an interference member distending from the assembly axis such that when the connector is in the first state, the interference member does not intersect the first hole in the first portion, and when the connector is in the second state, the interference member does at least in part intersect the first hole in the first portion; and
   an actuator coupled to the second portion and configured to transition the connector from the first state to the second state.

2. The connector of claim 1 wherein the center of the first hole is offset from the assembly axis by about 7 mm to 12 mm.

3. The connector of claim 1 wherein the first portion includes teeth with peeks and valleys that radiate away from the assembly axis and face toward the second portion.

4. The connector of claim 3 wherein the second portion includes teeth with peeks and valleys that radiate away from the assembly axis and face toward the first portion.

5. The connector of claim 1 wherein the second hole is an oblong hole.

6. The connector of claim 5 wherein a longer axis of the oblong hole is oriented at an angle to the assembly axis that is other than a right angle.

7. The connector of claim 1 wherein the interference member is tapered where the interference member intersects the first hole in the first portion.

8. The connector of claim 1 wherein the assembly is keyed to the first portion to substantially prevent rotation of the assembly about the assembly axis relative to the first portion.

9. The connector of claim 1 wherein the actuator is configured to press against a second linear element in the second hole to urge the connector from the first state to the second state.

10. A connector for coupling a first linear element to a second linear element comprising:
   a first portion through which an assembly axis passes, the first portion having a first hole that is configured to receive at least a part of the first linear element;
   a second portion through which the assembly axis passes, the second portion comprising:
      a body,
      a second hole through the body transverse to the assembly axis, the second hole being configured to receive at least a part of the second linear element, the second hole being larger than the second linear element to allow for lateral movement of the second linear element within the second hole, and
      a locking component coupled to the body and capable of sliding relative to the body along the assembly axis and including at least one bearing surface that at least in part intersects the second hole,
      wherein directed lateral movement of the second linear element within the second hole causes the second linear element to contact one or more of the at least one bearing surfaces and move the locking component along the assembly axis toward the first portion;
   an assembly that is positioned at least in part along the assembly axis within the first portion and the second portion and able to slide a limited distance within at least the first portion, the assembly having an interference member such that the interference member is capable of intersecting the first hole in the first portion when the assembly is slid in the first portion toward the second portion, the assembly being coupled between the first portion and the body of the second portion such that sliding separation of the first portion and the body of the second portion along the assembly axis is limited by the assembly, and wherein movement of the locking component relative to the body of the second portion against the first portion causes the limit of sliding separation between the first portion and the body of the second portion to be reached and causes the interference member to intersect the first hole in the first portion to thereby wedge the first linear element into a reentrant notch formed between the interference member and a wall of the first hole; and
   an actuator coupled to the second portion and configured to push against the second linear element to cause directed lateral movement of the second linear element within the second hole and to move the locking component along the assembly axis toward the first portion, and to wedge the second linear element into a reentrant notch formed between the at least one bearing surface and a plane or tangent to a point of contact of the second hole to lock the second linear element relative to the second portion;
   wherein the second portion is rotatable about the assembly axis relative to the first portion when the locking component has not been moved toward the locking component along the assembly axis to engage the first portion.

11. The connector of claim 10 wherein the first hole is offset from the assembly axis, and wherein the interference member distends from the assembly axis to be capable of intersecting with the first hole.

12. The connector of claim 10 wherein the first portion includes teeth with peeks and valleys that radiate away from the assembly axis and face toward the second portion and the second portion includes teeth with peeks and valleys that radiate away from the assembly axis and face toward the first portion.

13. The connector of claim 10 wherein the locking component is a washer that substantially circumscribes the assembly axis.

14. The connector of claim 13 wherein the washer includes one or more ramps that at least in part intersect the second hole, wherein when the second linear element is pressed against the one or more ramps, the washer is urged to move along the assembly axis relative to the body of the second portion.

15. The connector of claim 10 wherein the interference member is tapered where the interference member intersects the first hole in the first portion.

16. A system for spinal stabilization comprising:
one or more vertebral anchors for attaching to a vertebral body;
one or more spinal rods for supporting a spinal structure; and
one or more connectors for coupling the one or more vertebral anchors to the one or more spinal rods, at least one of the one or more connectors comprising:
a first portion through which an assembly axis passes, the first portion having a first hole that is configured to receive at least a part of the one or more vertebral anchors, and wherein the first hole is offset from the assembly axis;
a second portion through which the assembly axis passes, the second portion having a second hole configured to receive at least a part of the one or more spinal rods, and wherein the second portion is rotatable about the assembly axis relative to the first portion when the connector is in a first state and wherein the second portion is locked relative to the first portion when the connector is in a second state, the second portion includes a washer that substantially circumscribes the assembly axis and is slidingly coupled to other parts of the second portion, the washer includes one or more ramps that at least in part intersect the second hole in the second portion, wherein when the one or more spinal rods is pressed against the one or more ramps, the washer is urged to move along the assembly axis relative to the other parts of the second portion;
an assembly that is positioned at least in part along the assembly axis within the first portion and the second portion, the assembly having an interference member distending from the assembly axis such that when the connector is in the first state, the interference member does not intersect the first hole in the first portion, and when the connector is in the second state, the interference member does at least in part intersect the first hole in the first portion; and
an actuator coupled to the second portion and configured to transition the connector from the first state to the second state.

* * * * *